(12) United States Patent
Uribe et al.

(10) Patent No.: US 11,540,749 B2
(45) Date of Patent: Jan. 3, 2023

(54) SYSTEM AND METHOD FOR AUTOMATED DETECTION OF NEUROLOGICAL DEFICITS

(71) Applicants: University of Virginia Patent Foundation, Charlottesville, VA (US); Omar Uribe, Sterling, VA (US); Mark McDonald, Charlottesville, VA (US); Andrew M. Southerland, Charlottesville, VA (US); Gustavo Rohde, Crozet, VA (US); Yan Zhuang, Charlottesville, VA (US)

(72) Inventors: Omar Uribe, Sterling, VA (US); Mark McDonald, Charlottesville, VA (US); Andrew M. Southerland, Charlottesville, VA (US); Gustavo Rohde, Crozet, VA (US); Yan Zhuang, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 380 days.

(21) Appl. No.: 15/733,244

(22) PCT Filed: Jan. 22, 2019

(86) PCT No.: PCT/US2019/014605
§ 371 (c)(1),
(2) Date: Jun. 16, 2020

(87) PCT Pub. No.: WO2019/144141
PCT Pub. Date: Jul. 25, 2019

(65) Prior Publication Data
US 2021/0093231 A1   Apr. 1, 2021

Related U.S. Application Data

(60) Provisional application No. 62/620,096, filed on Jan. 22, 2018.

(51) Int. Cl.
*A61B 5/11* (2006.01)
*G06N 20/00* (2019.01)
(Continued)

(52) U.S. Cl.
CPC .......... *A61B 5/1128* (2013.01); *A61B 5/4076* (2013.01); *A61B 5/4803* (2013.01);
(Continued)

(58) Field of Classification Search
CPC ... A61B 5/1128; A61B 5/4076; A61B 5/4803; A61B 5/11; A61B 5/1103; G06F 3/013;
(Continued)

(56) References Cited

U.S. PATENT DOCUMENTS 10,262,196 B2 * 4/2019 Krishna Rao ........ A61B 5/4076
10,806,393 B2 * 10/2020 Einfalt ................. A61B 5/4088
(Continued)

OTHER PUBLICATIONS

International Search Report and Written Opinion dated Mar. 29, 2019, in International Application No. PCT/US2019/014605 (5pgs.).

*Primary Examiner* — John B Strege
(74) *Attorney, Agent, or Firm* — Finnegan, Henderson, Farabow, Garrett & Dunner LLP (57) ABSTRACT

The disclosed embodiments provide systems and methods for predicting presence of one or more neurological deficits. The system may include a microphone, a camera, one or more memory devices storing instructions, and one or more processors configured to execute the instructions to extract audio information including a period density entropy coefficient and a mel frequency cepstral coefficient from an audio feed received from the microphone. Additionally, the instructions may cause the processor to determine position and depth information of eye movement from a video feed received from the camera and detect features of interest
(Continued)

including facial landmarks, spatial orientation of limbs, and positional information of limb movements from the video feed. The one or more processors may further extract the features of interest from the video feed and process the extracted features of interest by aligning the extracted features of interest to a common reference.

20 Claims, 5 Drawing Sheets (51) Int. Cl.
    *A61B 5/00*     (2006.01)
    *G06F 3/01*     (2006.01)
    *G06V 40/16*     (2022.01)
(52) U.S. Cl.
    CPC ............. *G06F 3/013* (2013.01); *G06N 20/00* (2019.01); *G06V 40/171* (2022.01); *G06V 40/176* (2022.01)

(58) Field of Classification Search
CPC .... G06N 20/00; G06V 40/171; G06V 40/176; G06V 40/172; G06V 20/52
See application file for complete search history.

(56) References Cited

U.S. PATENT DOCUMENTS

| | | |
|---|---|---|
| 2011/0218253 A1 | 9/2011 | Lange et al. |
| 2012/0314064 A1* | 12/2012 | Liu ..................... G06V 20/52 |
| | | 348/143 |
| 2015/0112232 A1 | 4/2015 | Quatieri et al. |
| 2016/0022137 A1* | 1/2016 | Wetzel ................ A61B 5/4076 |
| | | 600/558 |
| 2017/0046569 A1 | 2/2017 | Krishna Rao et al. |
| 2017/0195637 A1* | 7/2017 | Kusens ............... A61B 5/0077 |
| 2019/0110754 A1* | 4/2019 | Rao ..................... G06N 20/00 |
| 2022/0249610 A1* | 8/2022 | Ziegelaar ............. A61K 45/06 |

* cited by examiner

SYSTEM AND METHOD FOR AUTOMATED DETECTION OF NEUROLOGICAL DEFICITS

PRIORITY CLAIM

This application is a U.S. national phase entry of International Application No. PCT/US2019/014605, filed Jan. 22, 2019, which claims priority under 35 U.S.C. § 119 to U.S. Provisional Application No. 62/620,096, filed Jan. 22, 2018, entitled "System, Method and Computer Readable Medium for Automated Detection of Neurological Defects," which is expressly incorporated herein by reference in its entirety.

TECHNICAL FIELD

The present disclosure provides systems and methods for detecting neurological deficits. In particular, in some embodiments, a machine-learning algorithm may predict a presence of one or more neurological deficits by classifying audio information, position and depth information of eye movement, a set of coordinates representing features of interest, and intensity-based features using a predictive model.

BACKGROUND

Early recognition and reduced time to treatment improves outcomes of stroke. Prehospital screening tools administered by emergency medical providers facilitate early detection and triage of acute stroke, but the accuracy and reliability of these tools in practice is variable. An automated screening tool with enhanced accuracy would minimize inter-operator variability and operator error and improve stroke outcomes by more rapid diagnosis and triage.

In the United States, stroke is a leading cause of death and disability with more than 795,000 people who suffer an incident stroke each year. Numerous studies have shown that reduction in time to treatment by as little as fifteen minutes significantly decreases mortality and disability in stroke patients. Recognition of stroke by EMS leads to earlier and more frequent treatment with tissue plasminogen activator (tPA). Implementation of prehospital stroke screening tools by EMS has been shown to improve detection of stroke in the prehospital setting. The most commonly used stroke screen is the Cincinnati Prehospital Stroke Scale, which assesses facial weakness, limb drift, and abnormal speech. However, detection of stroke deficits in the field is highly variable and operator dependent, contributing to limitations in sensitivity and specificity. Current systems which assesses facial weakness, limb drift, and abnormal speech are designed to be performed quickly on the field by trained emergency medical personnel. However, neurological deficits in stroke often present in various forms with varying degrees of severity requiring large amounts of exposure over time to more accurately and consistently recognize them. Areas with low population densities often rely on volunteers for their emergency services personnel for which training and field experience will vary significantly. Further, recent clinical trials support endovascular therapy conducted at highly specialized stroke centers for patients with large vessel occlusion acute ischemic stroke, and efforts are underway to validate new EMS screening tools to prioritize transport to hospitals with advanced intervention capability. Machine learning algorithms may iteratively learn from and make predictions about data without being explicitly programmed. Previous research has demonstrated that machine learning algorithms may accurately detect facial asymmetry, direction of gaze, limb drift, dysarthria, and language abnormalities. However, current systems fail to detect common neurological deficits in acute stroke patients through the analysis of video from smart phones, tablets, or other mobile devices.

In view of the shortcomings of current systems and methods for detecting neurological deficits, a system for enhancing accuracy of stroke detection and expediting triage and diagnosis related to stroke conditions is desired. More specifically, a mobile video assessment and automated screening tool system in a prehospital setting using a machine learning algorithm that accurately identifies facial weakness in static images and video and detects common clinical signs in neurological deficits using computational video analysis is desired. Such a system may provide clinical utility to any patient over 55 with one or more risk factors for stroke.

Using machine-learning algorithms, the system and method of the present disclosure constructs an automated screening tool for detection of stroke and large vessel occlusion in the prehospital setting that enhances (1) accuracy of prehospital stroke diagnosis, (2) timeliness of treatment with acute stroke therapies, and (3) appropriateness of selective triage to interventional capable comprehensive stroke centers.

SUMMARY

In the following description, certain aspects and embodiments of the present disclosure will become evident. It should be understood that the disclosure, in its broadest sense, could be practiced without having one or more features of these aspects and embodiments. It should also be understood that these aspects and embodiments are merely exemplary.

Disclosed embodiments provide systems for predicting presence of one or more neurological deficits. For example, certain embodiments may include one or more memory devices storing instructions and one or more processors configured to execute the instructions to extract audio information including a period density entropy coefficient and a mel frequency cepstral coefficient from an audio feed received from the microphone and determine position and depth information of eye movement from a video feed received from the camera. The one or more processors are further configured to detect features of interest including facial landmarks, spatial orientation of limbs, and positional information of limb movements from the video feed and extract the features of interest from the video feed. Additionally, the one or more processors are configured to process the extracted features of interest by aligning the extracted features of interest to a common reference and generate a set of coordinates representing the features of interest. The one or more processors are further configured to generate intensity-based features including a histogram of oriented gradients representing the extracted features of interest and provide the audio information, the position and depth information of eye movement, the set of coordinates representing the features of interest, and the intensity-based features to a predictive model to classify the audio information, the position and depth information of eye movement, the set of coordinates representing the features of interest, and the intensity-based features, and in response to the classification, predict a presence of one or more neurological deficits.

Disclosed embodiments provide computer-implemented methods for predicting the presence of one or more neurological deficits. For example, certain embodiments of computer-implemented methods may include extracting audio information including a period density entropy coefficient and a mel frequency cepstral coefficient from an audio feed, determining position and depth information of eye movement from a video feed, and detecting features of interest including facial landmarks, spatial orientation of limbs, and positional information of limb movement from the video feed. Certain embodiments may further include extracting the features of interest from the video feed and processing the extracted features of interest by aligning the features of interest to a common reference. Computer-implemented methods may include generating a set of coordinates representing the features of interest, generating intensity-based features including a histogram of oriented gradients representing the extracted features of interest providing the audio information, the position and depth information of eye movement, the set of coordinates representing the features of interest, and the intensity-based features to a predictive model to classify the audio information, the position and depth information of eye movement, the set of coordinates representing the features of interest, and the intensity-based features, and in response to the classification, predicting a presence of one or more neurological deficits.

Disclosed embodiments provide non-transitory computer-readable medium storing instructions that, when executed by one or more processors, cause the one or more processors to perform operations for predicting presence of one or more neurological deficits. For example, certain embodiments may include extracting audio information including a period density entropy coefficient and a mel frequency cepstral coefficient from an audio feed, determining position and depth information of eye movement from a video feed, and detecting features of interest including facial landmarks, spatial orientation of limbs, and positional information of limb movement from the video feed. Furthermore, certain embodiments may include extracting the features of interest from the video feed and processing the extracted features of interest by aligning the extracted features of interest to a common reference. Some embodiments may include generating a set of coordinates representing the features of interest, generating intensity-based features including a histogram of oriented gradients representing the extracted features of interest providing the audio information, the position and depth information of eye movement, the set of coordinates representing the features of interest, and the intensity-based features to a predictive model to classify the audio information, the position and depth information of eye movement, the set of coordinates representing the features of interest, and the intensity-based features, and in response to the classification, predicting a presence of one or more neurological deficits.

In accordance with additional embodiments of the present disclosure, a computer-readable medium is disclosed that stores instructions that, when executed by a processor(s), causes the processor(s) to perform operations consistent with one or more disclosed methods.

The foregoing general description and the following detailed description are exemplary and explanatory only and are not restrictive of the claims.

It is to be understood that both the foregoing general description and the following detailed description are exemplary and explanatory only, and are not restrictive of the disclosed embodiments, as claimed.

BRIEF DESCRIPTION OF THE DRAWINGS

The accompanying drawings, which are incorporated in and constitute a part of this specification, illustrate several embodiments and, together with the description, serve to explain the disclosed principles. In the drawings.

DESCRIPTION OF THE EMBODIMENTS

Reference will now be made in detail to exemplary embodiments, examples of which are illustrated in the accompanying drawings and disclosed herein. Wherever convenient, the same reference numbers will be used throughout the drawings to refer to the same or like parts.

As described in further detail herein, the disclosed embodiments are directed to systems, methods, and computer readable medium for predicting the presence of one or more neurological deficits.

Figure 1:
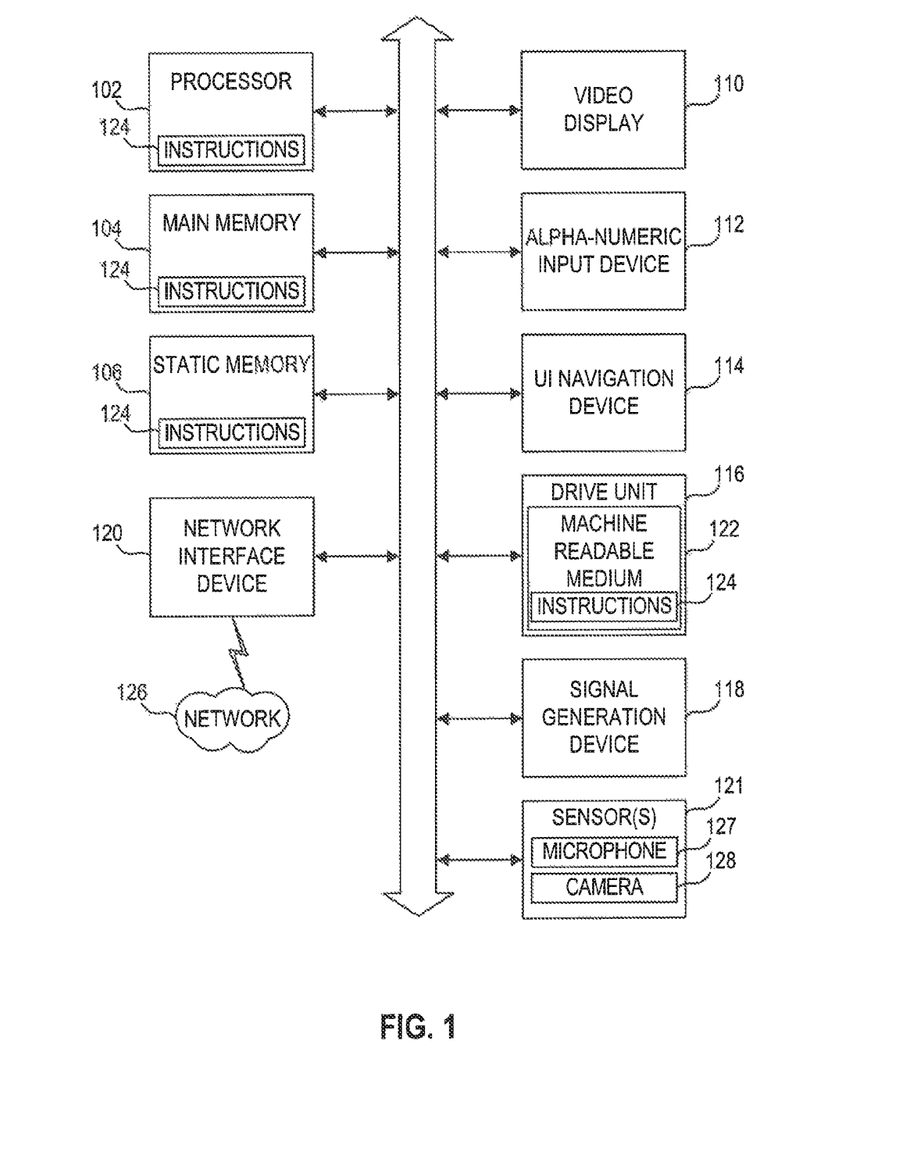
FIG. 1 is a block diagram of an exemplary system, consistent with disclosed embodiments.

FIG. 1 shows a block diagram of an exemplary system 100 upon which one or more embodiments (e.g., discussed methodologies) may be implemented (e.g., run).

Examples of system 100 may include logic, one or more components, circuits (e.g., modules), or mechanisms. Circuits are tangible entities configured to perform certain operations. In an example, circuits may be arranged (e.g., internally or with respect to external entities such as other circuits) in a specified manner. In an example, one or more computer systems (e.g., a standalone, client or server computer system) or one or more hardware processors (processors) may be configured by software (e.g., instructions, an application portion, or an application) as a circuit that operates to perform certain operations as described herein. In an example, the software may reside (1) on a non-transitory machine readable medium or (2) in a transmission signal. In an example, the software, when executed by the underlying hardware of the circuit, causes the circuit to perform the certain operations.

In one embodiment, a circuit may be implemented mechanically or electronically. For example, a circuit may comprise dedicated circuitry or logic that is specifically configured to perform one or more techniques such as discussed above, including, for example, a special-purpose processor, a field programmable gate array (FPGA) or an application-specific integrated circuit (ASIC). In an example, a circuit may comprise programmable logic (e.g., circuitry, as encompassed within a general-purpose processor or other programmable processor) that may be temporarily configured (e.g., by software) to perform the certain operations. The decision to implement a circuit mechanically (e.g., in dedicated and permanently configured circuitry), or in temporarily configured circuitry (e.g., configured by software) may be driven by cost and time considerations.

Accordingly, the term "circuit" is understood to encompass a tangible entity, be that an entity that is physically constructed, permanently configured (e.g., hardwired), or temporarily (e.g., transitorily) configured (e.g., programmed) to operate in a specified manner or to perform specified operations. In an example, given a plurality of temporarily configured circuits, each of the circuits need not be configured or instantiated at any one instance in time. For example, where the circuits comprise a general-purpose processor configured via software, the general-purpose processor may be configured as respective different circuits at different times. Software may accordingly configure a processor, for example, to constitute a particular circuit at one instance of time and to constitute a different circuit at a different instance of time.

In an example, circuits may provide information to, and receive information from, other circuits. In this example, the circuits may be regarded as being communicatively coupled to one or more other circuits. Where multiple of such circuits exist contemporaneously, communications may be achieved through signal transmission (e.g., over appropriate circuits and buses) that connect the circuits. In embodiments in which multiple circuits are configured or instantiated at different times, communications between such circuits may be achieved, for example, through the storage and retrieval of information in memory structures to which the multiple circuits have access. For example, one circuit may perform an operation and store the output of that operation in a memory device to which it is communicatively coupled. A further circuit may then, at a later time, access the memory device to retrieve and process the stored output. In an example, circuits may be configured to initiate or receive communications with input or output devices and may operate on a resource (e.g., a collection of information).

The various operations of method examples described herein may be performed, at least partially, by one or more processors that are temporarily configured (e.g., by software) or permanently configured to perform the relevant operations. Whether temporarily or permanently configured, such processors may constitute processor-implemented circuits that operate to perform one or more operations or functions. In an example, the circuits referred to herein may comprise processor-implemented circuits.

Similarly, the methods described herein may be at least partially processor-implemented. For example, at least some of the operations of a method may be performed by one or more processors or processor-implemented circuits. The performance of certain of the operations may be distributed among the one or more processors, not only residing within a single machine, but deployed across a number of machines. In an example, the processor or processors may be located in a single location (e.g., within a home environment, an office environment or as a server farm), while in other examples the processors may be distributed across a number of locations.

The one or more processors may also operate to support performance of the relevant operations in a "cloud computing" environment or as a "software as a service" (SaaS). For example, at least some of the operations may be performed by a group of computers (as examples of machines including processors), with these operations being accessible via a network (e.g., the Internet) and via one or more appropriate interfaces (e.g., Application Program Interfaces (APIs).)

Example embodiments (e.g., apparatus, systems, or methods) may be implemented in digital electronic circuitry, in computer hardware, in firmware, in software, or in any combination thereof. Example embodiments may be implemented using a computer program product (e.g., a computer program, tangibly embodied in an information carrier or in a machine readable medium, for execution by, or to control the operation of, data processing apparatus such as a programmable processor, a computer, or multiple computers).

A computer program may be written in any form of programming language, including compiled or interpreted languages, and it may be deployed in any form, including as a stand-alone program or as a software module, subroutine, or other unit suitable for use in a computing environment. A computer program may be deployed to be executed on one computer or on multiple computers at one site or distributed across multiple sites and interconnected by a communication network.

In an example, operations may be performed by one or more programmable processors executing a computer program to perform functions by operating on input data and generating output. Examples of method operations may also be performed by, and example apparatus may be implemented as, special purpose logic circuitry (e.g., a field programmable gate array (FPGA) or an application-specific integrated circuit (ASIC)).

The computing system may include clients and servers. A client and server are generally remote from each other and generally interact through a communication network. The relationship of client and server arises by virtue of computer programs running on the respective computers and having a client-server relationship to each other. In embodiments deploying a programmable computing system, it may be appreciated that both hardware and software architectures require consideration. Specifically, it may be appreciated that the choice of whether to implement certain functionality in permanently configured hardware (e.g., an ASIC), in temporarily configured hardware (e.g., a combination of software and a programmable processor), or a combination of permanently and temporarily configured hardware may be a design choice. Below are set out hardware (e.g., system 100 disclosing a machine) and software architectures that may be deployed in example embodiments.

In some embodiments, system 100 may be operable as a standalone device or system 100 may be connected (e.g., networked) to other machines or systems.

In a networked deployment, the system 100 may operate in the capacity of either a server or a client machine in server-client network environments. In an example, system 100 may act as a peer machine in peer-to-peer (or other distributed) network environments. System 100 may be a personal computer (PC), a tablet PC, a set-top box (STB), a Personal Digital Assistant (PDA), a mobile telephone, a web appliance, a network router, switch or bridge, or any machine capable of executing instructions (sequential or otherwise) specifying actions to be taken (e.g., performed) by system 100. In some embodiments, system 100 may be a smart phone, tablet, laptop, desktop, smart mirror, mobile device, or any system capable of providing a teleneurological automated screening tool. Further, while only a single system 100 is illustrated, the term "system" shall also be taken to include any machine, any collection of machines that individually or jointly execute a set (or multiple sets) of instructions to perform any one or more of the methodologies discussed herein.

Example system (e.g., computer system) 100 may include a processor 102 (e.g., a central processing unit (CPU), a graphics processing unit (GPU) or both), a main memory 104 and a static memory 106, some or all of which may communicate with each other via a bus 108. The system 100 may further include a display unit 110, an alphanumeric input device 112 (e.g., a keyboard), and a user interface (UI) navigation device 111 (e.g., a mouse). In an example, the display unit 110, input device 117 and UI navigation device 114 may be a touch screen display. The system 100 may additionally include a storage device (e.g., drive unit) 116, a signal generation device 118 (e.g., a speaker), a network interface device 120, and one or more sensors 121, such as a global positioning system (GPS) sensor, compass, accelerometer, microphone 127, camera 128, or other sensor.

The storage device 116 may include a machine readable medium 122 on which is stored one or more sets of data structures or instructions 124 (e.g., software) embodying or utilized by any one or more of the methodologies or functions described herein. The instructions 124 may also reside, completely or at least partially, within the main memory 104, within static memory 106, or within the processor 102 during execution thereof by the system 100. In an example, one or any combination of the processor 102, the main memory 104, the static memory 106, or the storage device 116 may constitute machine readable media. In some embodiments, instructions 124 may include a set of machine learning algorithms.

While the machine readable medium 122 is illustrated as a single medium, the term "machine readable medium" may include a single medium or multiple media (e.g., a centralized or distributed database, and/or associated caches and servers) that configured to store the one or more instructions 124. The term "machine readable medium" may also be taken to include any tangible medium that is capable of storing, encoding, or carrying instructions for execution by the machine and that cause the machine to perform any one or more of the methodologies of the present disclosure or that is capable of storing, encoding or carrying data structures utilized by or associated with such instructions. The term "machine readable medium" may accordingly be taken to include, but not be limited to, solid-state memories, and optical and magnetic media. Specific examples of machine readable media may include non-volatile memory, including, by way of example, semiconductor memory devices (e.g., Electrically Programmable Read-Only Memory (EPROM), Electrically Erasable Programmable Read-Only Memory (EEPROM)) and flash memory devices; magnetic disks such as internal hard disks and removable disks; magneto-optical disks; and CD-ROM and DVD-ROM disks.

Instructions 124 may further be transmitted or received over a communications network 126 using a transmission medium via the network interface device 120 utilizing any one of a number of transfer protocols (e.g., frame relay, IP, TCP, UDP, HTTP, etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., IEEE 802.11 standards family known as Wi-Fi®, IEEE 802.16 standards family known as WiMax®), peer-to-peer (P2P) networks, among others. The term "transmission medium" shall be taken to include any intangible medium that is capable of storing, encoding or carrying instructions for execution by the machine, and includes digital or analog communications signals or other intangible medium to facilitate communication of such software.

In some embodiments, system 100 includes (1) a set of machine learning algorithms (implemented with a system, method and computer readable medium) that detect observable neurological deficits consisting of pathologically asymmetric smile, pathologically asymmetric eyebrow raise, limb ataxia (incoordination), limb drift, pronator drift (inward turning of the arm from a palm-up starting position), and nystagmus (abnormal eye movements) from a video feed, (2) a machine learning algorithm (implemented with a system, method and computer readable medium) that detects speech pathology such as dysarthria (slurred speech) from an audio feed, (3) a tracking algorithm (implemented with a system, method and computer readable medium) to determine positional information of eye movement to determine gaze preference from a video feed, and (4) a comprehensive algorithm (implemented with a system, method and computer readable medium) that uses the individual deficit detection and tracking algorithms to predict the presence of stroke from a video feed.

The algorithms and techniques (implemented with a system, method and computer readable medium) may detect focal neurological deficits by extracting features of interest (i.e. including facial landmarks including face and eye positions and key points of the limbs) from the subject. This information may be preprocessed (facial landmarks/limb key points alignment and segmentation) to remove confounds such as head position and orientation. To capture changes in the subject's facial landmark movement, facial configural features may be calculated and fed to a support vector machine classifier for classification. Facial landmarks may also provide information on face position which may be used to estimate the position of the eyes. Gaze-related information such as angle, velocities, and symmetries may be calculated using an eyeball model and abnormal movements may be determined by positional tracking. Limb ataxia may be determined by tracking the variation in pixel intensity on a region of interest around the nose with a more erratic pattern showing higher and more frequent variations. In some embodiments, system 100 may generate intensity-based features including a histogram of oriented gradients representing the extracted features of interest. For the dysarthria detection, the features of an audio signal may include a recurrence period density entropy coefficient and a mel frequency cepstral coefficient that may be extracted from the audio feed and provided to a predictive model for dysarthria detection. The individual algorithms may be executed simultaneously and their output may be fed into a predictive model algorithm trained in the detection of acute stroke.

In some embodiments, the machine learning algorithms and techniques may not be developed in isolation from the data they analyze. The type and quality of the data collected influence the structure of the code, as well as the performance of the algorithm. In an example, the database used for this project consists of videos of stroke patients performing various tasks to elicit neurological deficits, if present. Patients are filmed holding their arms outstretched in front of them with palms facing up for ten seconds, a drift from this position could indicate muscle weakness. Patients are asked to hold their arms outstretched in front of them and quickly touch their nose with their right index finger and return to the starting position. The test is repeated with the left hand. An erratic path of the finger as it travels to the nose may indicate trouble with coordination. Patients are asked to smile, show their teeth, and raise their eyebrows—asymmetry in these movements may indicate facial weakness. Patients are asked to look as far left and as far right as they can, abnormal eye movements may be detected during these movements. Patients are asked to repeat two phrases to look for signs or patterns in their speech signaling an abnormality. The techniques used to create these algorithms require the training data to be labeled into distinct categories, for the purposes of this study: normal and pathologic. The data will be labeled according to the diagnosis found using clinical findings and confirmatory imaging. Correct labeling of the training data is critical to optimize feature extraction between the two groups. Incorrect labeling of training data may lead to erroneous extraction of distinguishing features and significant reduction in the overall performance.

In some embodiments, system 100 may provide an ability to encode neurological expertise into a set of algorithms that may be used to perform a reproducible stroke assessment without requiring the presence of a trained neurologist. In some embodiments, system 100 may be used in the pre-hospital evaluation of stroke patients.

An embodiment of the present invention provides automating the screening process that in turn reduces the subjectivity of the assessment and the dependency on operator training and experience. In an example, automation may be achieved through supervised and deep learning algorithms along with large amounts of training data to build models classifying videos or images into normal or abnormal depending on presenting features. With use and exposure to more data, these algorithms may adjust their internal parameters to increase their accuracy by creating better predictive models. Thus, these algorithms (implemented with a system, method and computer readable medium) may have higher accuracy, sensitivity, and specificity for predicting stroke than current screens.

Additionally, in an example, in order to detect a difference in an exam, the algorithm must calculate certain parameters, it may quantify the degree of asymmetry or difference found during examination as a percentage or relative measure based on these calculations, introducing a more objective and reproducible way to measure neurological deficits. By quantifying the degree or extent of the deficit, these algorithms (implemented with a system, method and computer readable medium) may establish thresholds beyond which detection is no longer possible for humans.

Conversely, an embodiment of the present invention provides that these thresholds may be used in training providers on the visual detection of neurological deficits based on objective measures and large amounts of previously acquired data. A digital medium also allows system 100 to build quality checks into the automated screen to ensure the examination was adequate for the detection algorithms to reliably predict the presence of stroke. These checks may be in the form of guiding parameters displayed during the examination and real-time feedback as the data is processed and an assessment is made.

These algorithms may provide a way to obtain and assess clinical data in a manner never utilized before. Currently, neurological deficits are evaluated in a qualitative manner based on the provider's experience. They are classified in discrete categories which often are too broad to properly capture the full spectrum of disease. In contrast, an aspect of an embodiment of the present invention provides, algorithms that are a novel way to recognize and quantify the degree of pathology present in a subject based on large amounts of data. By automating the detection of neurological deficits and integrating them into a stroke screen, an aspect of an embodiment provides for reproducing neurological expertise in a digital medium to be distributed and accessed wherever and whenever needed.

An aspect of an embodiment of the present invention provides, an automated stroke and large vessel occlusion screening system to be used by paramedics, bystanders, or ED providers in the acute setting to improve decisions about triage and management of the patient. In some embodiments, camera 128 of system 100 may be adapted for use in health surveillance. In such an embodiment, detecting signs of a subtle, chronic stroke may indicate the need for further diagnostic work-up in order to confirm the stroke and characterize the stroke mechanism. Identifying the presence of a chronic stroke may lead to significant changes in the clinical management of the patient such as surgical intervention in the case of carotid disease or patent foramen ovale (PFO), new risk classification in patients with atrial fibrillation or hyperlipidemia possibly leading to addition of new medications (antiplatelet or anticoagulant) for secondary stroke prevention.

Early recognition and treatment of stroke improves outcomes. Pre-hospital screening tools offer promise for early detection of acute stroke but have inconsistent performance. Exemplary system 100, an embodiment of the disclosed automated screening tool, may minimize inter-operator variability and operator error facilitating a rapid and reliable screen. Exemplary disclosed machine learning algorithms may assist in the detection of pathologic facial weakness using computational visual analysis.

Figure 2:
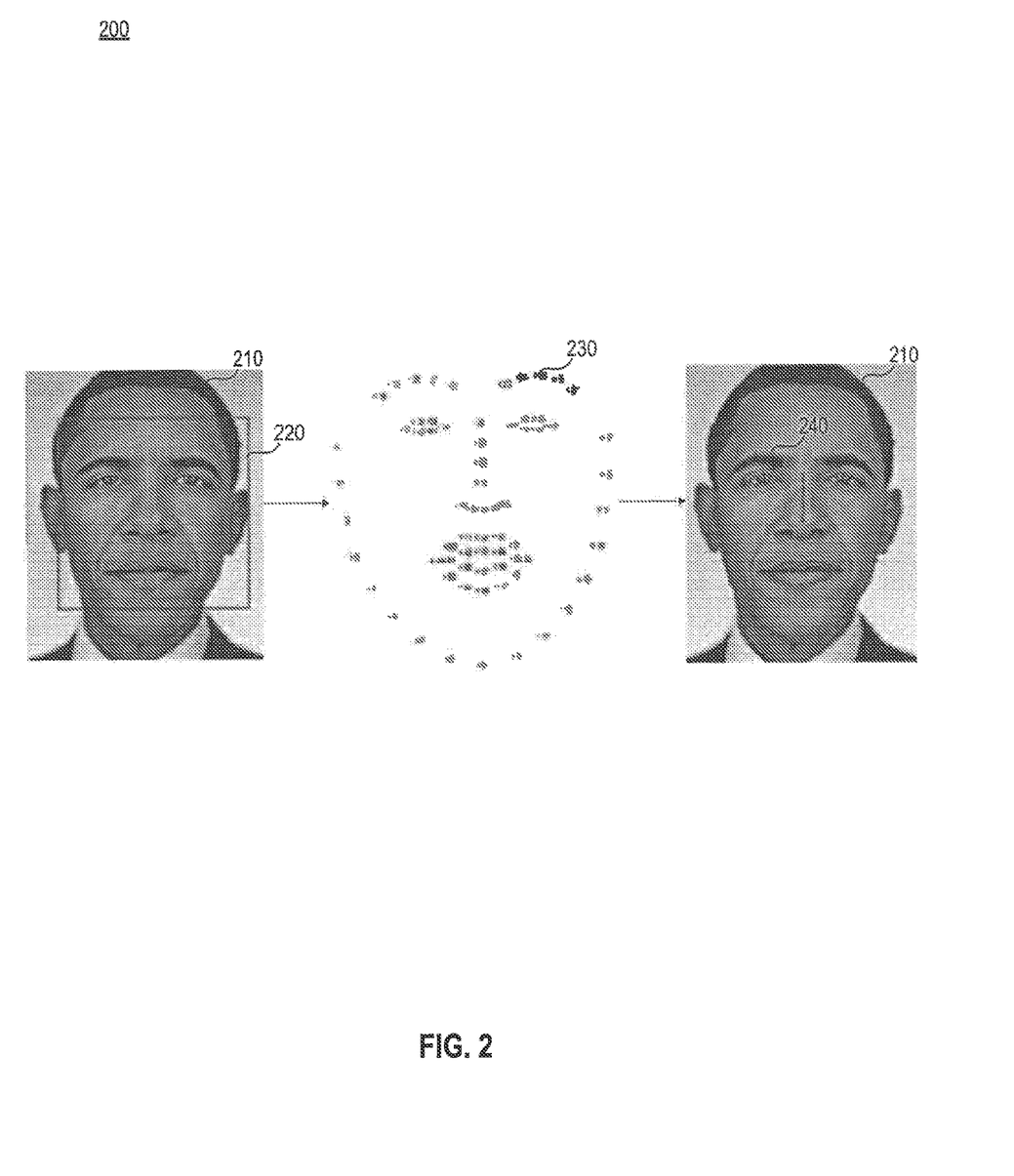
FIG. 2 is a block diagram of an exemplary facial landmark extraction, consistent with disclosed embodiments.

FIG. 2 is a block diagram of an exemplary facial landmark extraction process, consistent with disclosed embodiments. Process 200 may utilize a facial tracking code that forms a red rectangle, facial detection indicator 220, encompassing the area of patient 210's face. Process 200 conducts facial landmark extraction, extracting facial features of patient 210 represented by tracked facial coordinates 230 which includes coordinates of patient 210's eyes, eyebrows, nose, mouth, and perimeter of patient 210's face. In some embodiments, tracked facial coordinates 230 may further include eyeglasses, hairline, moles, wrinkles, ears, or any distinct feature on or around the face depicted in an image or video. Facial coordinates 240 of patient 210 include tracked facial coordinates 230 overlaid on an image of patient 210. In some embodiments, spatial orientation of limbs and limb movements may be extracted using process 200.

In some embodiments, system 100 may detect facial weakness, gaze preference, and limb weakness of patient 210 using a video recorded on a HIPAA-secure mobile video device.

In some embodiments, open source software may be used for the extraction of facial landmarks, eye position, and key points of limbs. Calculated facial configural features, including eye position, as well as limb symmetry comparisons may be fed to a support vector machine classifier for gaze-deviation, and face and limb weakness detection. In some embodiments, a tracking algorithm determines positional information of eye movement to determine gaze preference, skew deviation, abnormal fixation, and nystagmus. In some embodiments, system 100 may evaluate performance of algorithms using a 5-fold cross validation scheme and calculates sensitivity, specificity, and accuracy.

Figure 3:
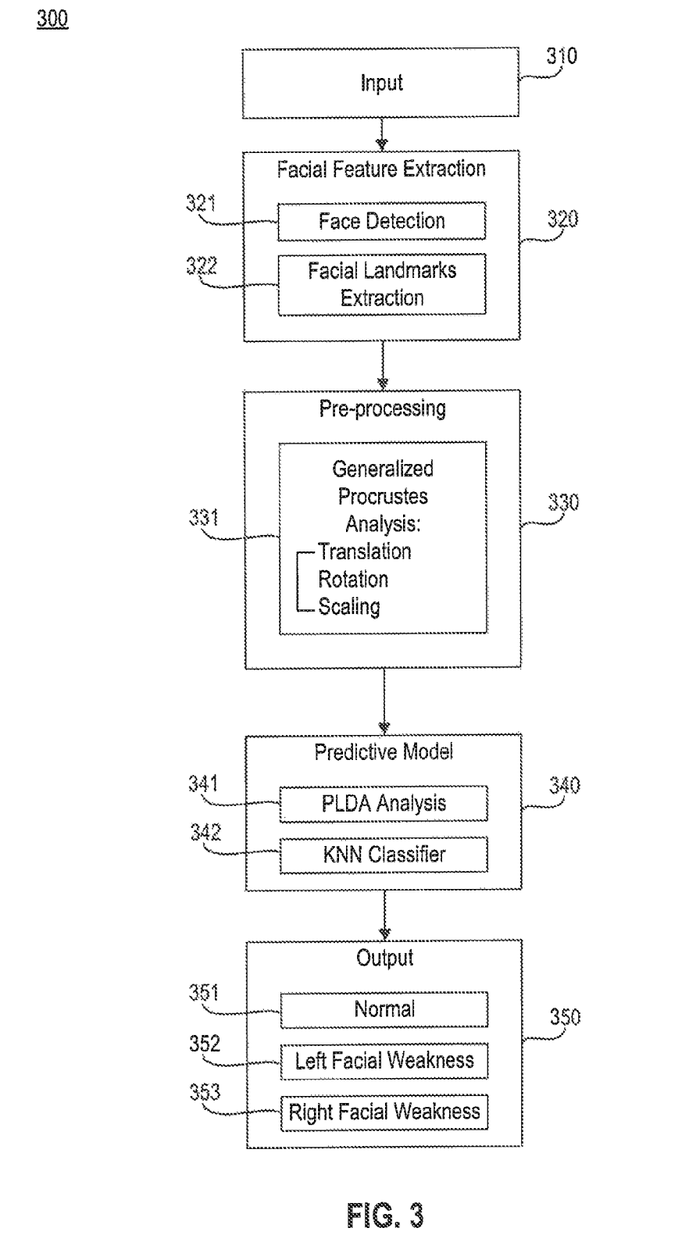
FIG. 3 is a block diagram of an exemplary algorithmic process for automated detection of neurological deficits, consistent with disclosed embodiments.

FIG. 3 is a block diagram of an exemplary algorithmic process for automated detection of neurological deficits, consistent with disclosed embodiments.

During process 300, input 310, such as images or video, may be input to facial feature extraction 320.

Process 300 may further include detecting features of interest including facial landmarks from the video feed. Facial feature extraction 320 may include face detection 321, also described in FIG. 2 where facial detection indicator 220 provides a red rectangle over patient's face. Facial feature extraction 320 may further include facial landmark extraction 322, which may include finding landmarks of the face such as the nose or the eyes. As discussed above, facial landmark extraction 322 is represented by tracked facial coordinates 230.

Process 300 may further include detecting features of interest including limbs, spatial orientation of limbs, and positional information of limb movements from the video feed. Limb detection is further described in FIG. 4B.

Pre-processing 330 takes extracted landmarks and aligns them to a common reference. In some embodiments, position of the head does not matter, process 300 may align extracted landmarks to a common reference to remove any orientation, head sizes, distance of head from camera which would increase space between landmarks. In some embodiments, the output of pre-processing 331 is a set of coordinates, such as facial coordinates 240 of FIG. 2, that may be input to the predictive model. In some embodiments, 60 or more coordinates of key landmarks, such as facial coordinates 240 of FIG. 2, of the face may be input to the predictive model. Pre-processing 330 may further include aligning limb landmarks.

Predictive model 340 may receive as input and may classify the inputs differently. In some embodiments, predictive model 340 may receive input landmark data, such as facial coordinates 240, and determine whether the data fits a certain category using a support vector machine, PLDA analysis 341, KNN classifier 342, and other classifying techniques. Predictive model 340 may output a category, such as class 1—normal, class 2—left facial weakness, or class 3—right facial weakness. Predictive model 340 may output a category, such as class 1—normal, class 2—left facial weakness, or class 3—right facial weakness, based on positional information of eye movement, and set of coordinates representing the features of interest (including facial features).

Process 300 further includes additional classifiers to classify limb coordinates from limb landmarks. In some embodiments, such a classifier may output a category, such as class1—normal, class 2—abnormal, based on the limb coordinates and limb landmarks.

Process 300 further includes additional classifiers to classify speech pathology. In some embodiments, such a classifier may output a category, such as class 1—normal, class 2—abnormal, based on the speech pathology, e.g., audio information including a period density entropy coefficient and a mel frequency cepstral coefficient from audio feed received from microphone 127 of FIG. 1.

In some embodiments, system 100 may feed calculated facial configural features, including facial landmarks and/or intensity values that describe the face, to at least one of a support vector machine classifier, penalized linear discriminant analysis classifier, k-nearest neighbors classifier, shallow neural networks classifier, deep neural networks classifier, and other classifiers for gaze-deviation and face and limb weakness detection.

Outputs 350 of the predictive model 340 may include normal 351, left facial weakness 352, and right facial weakness 353. In some embodiments, facial weakness may include, paralysis of muscle that controls activation of the face, asymmetry of the face, difficulty closing eye, flattening of the face where wrinkles are lost, inability to puff cheeks out, inability to keep the lips sealed, liquid or food dribbling on one side of mouth, food falling out of mouth, etc. In some embodiments, the system may provide both left facial weakness 352 and right facial weakness 353 as outputs.

In some embodiments, other outputs of the predictive model may include neurological diagnosis, type of stroke, location of stroke (i.e. stroke in the brain or nervous system), notification to a user, telemedicine specialist, or doctor connected remotely, emergency notification, or automated 911 alert etc.

In some embodiments, system 100 is an automatic pathological facial weakness detection system that may take a static image as the input and may output the facial weakness classification result, such as left facial weakness, right facial weakness, and normal. Given an image, system 100 may perform face detection and may extract the facial landmarks using open-source software packages. In a face normalization step, system 100 may align the extracted landmarks to a template to handle different face scales, location, and orientation in the input image using the Generalized Procrustes Analysis. The same normalization may be applied to intensity values. Only the near mouth region in which facial weakness is manifested is segmented. Then, intensity-based features, such as the Histogram of Oriented Gradient (HOG), may be extracted. The Principle Component Analysis (PCA) may be performed on a training dataset to reduce the feature dimension and to avoid the problem of overfitting. Finally, a predictive model, consisting of extracting a low dimensional embedding for each set of features via pLDA analysis, may classify the input as left facial weakness, normal, or right facial weakness. In such an embodiment, the above process may be performed with a video input as well, in which the above process is performed for each frame and a bag-of-words voting algorithm may be used to classify an entire video as normal or having left or right weakness.

In some embodiments, a front-end user interface may enable a user to interact with software, for example, by permitting the user to start the testing and by displaying the test outcome for the user to view, and a back-end may implement the proposed algorithm. In such an embodiment, the face tracking algorithm may use the open-source software. In some embodiments, pre-processing may include face alignment, mouth segmentation, and feature extraction and a predictive model may be in Python 2.7.

Figure 4A:
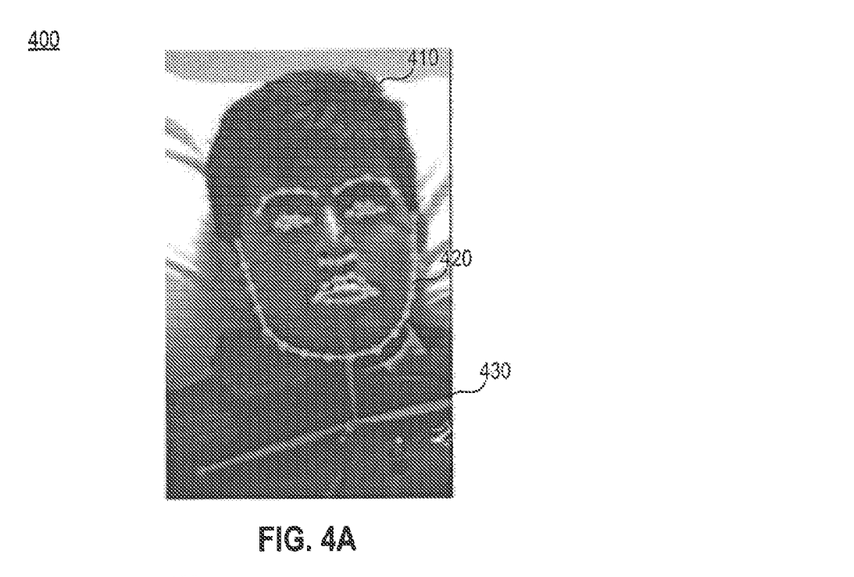
FIG. 4A is an image demonstrating facial landmarks and key points of the limbs extracted via computer vision techniques, consistent with disclosed embodiments.

FIG. 4A is an image demonstrating facial landmarks and key points of the limbs extracted via computer vision techniques, consistent with disclosed embodiments. For example, image 400 displays patient 410 as well as patient 410's facial coordinates 420 and patient 410's limb coordinates 430 via computer vision techniques. In some embodiments limb coordinates 430 display the spatial orientation of patient 410's limbs and positional information of patient 410's limb movement.

Figure 4B:
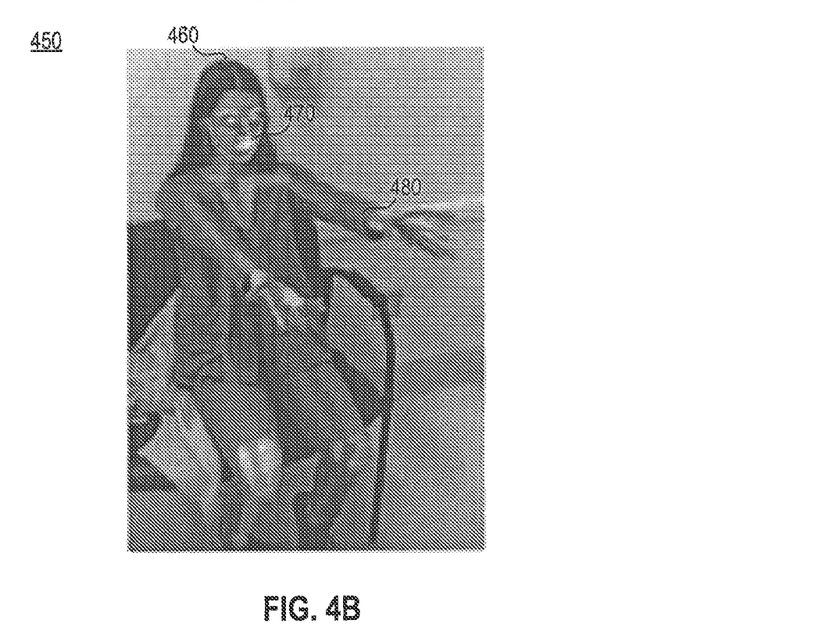
FIG. 4B is a second image demonstrating facial landmarks and key points of the limbs extracted via computer vision techniques, consistent with disclosed embodiments.

FIG. 4B is a second image demonstrating facial landmarks and key points of the limbs extracted via computer vision techniques, consistent with disclosed embodiments. For example, image 450 displays patient 450 as well as patient 450's facial coordinates 470 and patient 450's limb coordinates 480 via computer vision techniques. In some embodiments limb coordinates 480 display the spatial orientation of patient 450's limbs and positional information of patient 450's limb movement.

Figure 5:
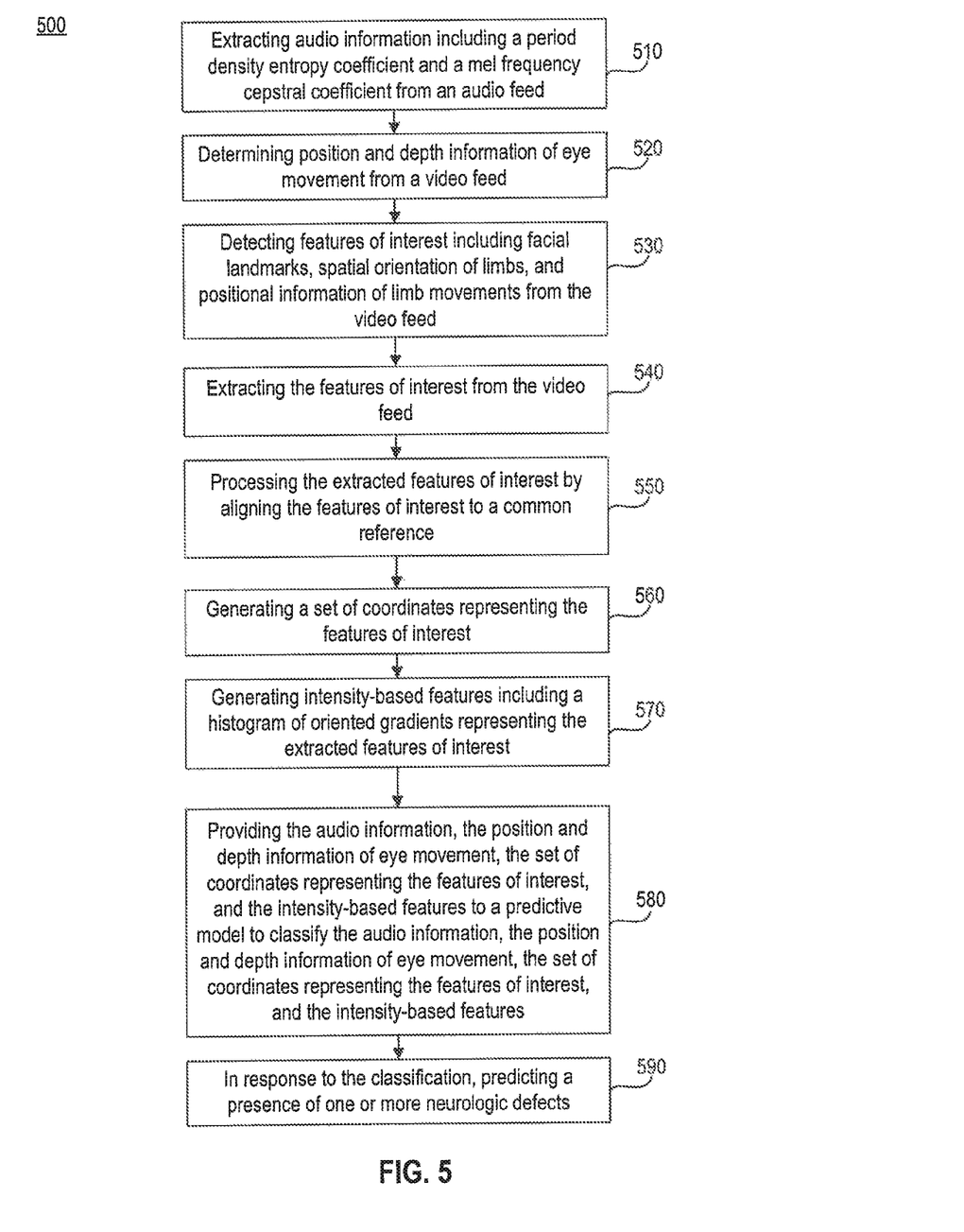
FIG. 5 is a block diagram of an exemplary process for automated detection of neurological deficits, consistent with disclosed embodiments.

FIG. 5 is a block diagram of an exemplary process for automated detection of neurological deficits, consistent with disclosed embodiments. Process 500 may be performed by processor 102 of, for example, system 100, which executes instructions 124 encoded on a computer-readable medium storage device. It is to be understood, however, that one or more steps of process 500 may be implemented by other components of system 100 (shown or not shown).

At step 510, system 100 may extract audio information including a period density entropy coefficient and a mel frequency cepstral coefficient from an audio feed received from microphone 127.

At step 520, system 100 may determine position and depth information of eye movement from video feed received from camera 128.

At step 530, system 100 may detect features of interest including facial landmarks, spatial orientation of limbs, and positional information of limb movements from the video feed received from camera 128. In some embodiments, steps 510, 520, and 530 occur in parallel (not shown).

At step 540, system 100 may extract features of interest from the video feed received from camera 128.

At step 550, system 100 may process the extracted features of interest by aligning the extracted features of interest to a common reference.

At step 560, system 100 may generate a set of coordinates representing the features of interest.

At step 570, system 100 may generate intensity-based features including a histogram of oriented gradients representing the extracted features of interest.

At step 580, system 100 may provide the audio information, the position and depth information of eye movement, the set of coordinates representing the features of interest, and the intensity-based features to a predictive model to classify the audio information, the position and depth information of eye movement, the set of coordinates representing the features of interest, and the intensity-based features. At step 590, in response to the classification of step 580, system 100 may predict a presence of one or more neurological deficits.

The foregoing description has been presented for purposes of illustration. It is not exhaustive and is not limited to the precise forms or embodiments disclosed. Modifications and adaptations of the embodiments will be apparent from consideration of the specification and practice of the disclosed embodiments. For example, the described implementations include hardware and software, but systems and methods consistent with the present disclosure may be implemented as hardware alone.

Computer programs based on the written description and methods of this specification are within the skill of a software developer. The various programs or program modules may be created using a variety of programming techniques. For example, program sections or program modules may be designed in or by means of Java™, C, C++, assembly language, or any such programming languages. One or more of such software sections or modules may be integrated into a computer system, non-transitory computer-readable media, or existing communications software.

Moreover, while illustrative embodiments have been described herein, the scope includes any and all embodiments having equivalent elements, modifications, omissions, combinations (e.g., of aspects across various embodiments), adaptations or alterations based on the present disclosure. The elements in the claims are to be interpreted broadly based on the language employed in the claims and not limited to examples described in the present specification or during the prosecution of the application, which examples are to be construed as non-exclusive. Further, the steps of the disclosed methods may be modified in any manner, including by reordering steps or inserting or deleting steps. It is intended, therefore, that the specification and examples be considered as exemplary only, with a true scope and spirit being indicated by the following claims and their full scope of equivalents.

What is claimed is:

1. A system for predicting presence of one or more neurological deficits, comprising:
   a microphone;
   a camera;
   one or more memory devices storing instructions; and
   one or more processors configured to execute the instructions to:
      extract audio information including a period density entropy coefficient and a mel frequency cepstral coefficient from an audio feed received from the microphone;
      determine position and depth information of eye movement from a video feed received from the camera;
      detect features of interest including facial landmarks, spatial orientation of limbs, and positional information of limb movements from the video feed;
      extract the features of interest from the video feed;
      process the extracted features of interest by aligning the extracted features of interest to a common reference;
      generate a set of coordinates representing the features of interest;
      generate intensity-based features including a histogram of oriented gradients representing the extracted features of interest;
      provide the audio information, the position and depth information of eye movement, the set of coordinates representing the features of interest, and the intensity-based features to a predictive model to classify the audio information, the position and depth information of eye movement, the set of coordinates representing the features of interest, and the intensity-based features; and
      in response to the classification, predict a presence of one or more neurological deficits.

2. The system of claim 1, wherein the system is a smart phone, tablet, laptop, desktop, smart mirror, or mobile device.

3. The system of claim 1, wherein the instructions include a set of machine learning algorithms.

4. The system of claim 1, wherein the one or more neurological deficits include at least one of asymmetric smile, asymmetric eyebrow raise, limb ataxia, limb drift, pronator drift, nystagmus, or stroke information including type of stroke and location of stroke.

5. The system of claim 1, wherein extracting audio information includes detecting speech pathology including at least one of speech disturbance and language disturbance.

6. The system of claim 1, wherein a tracking algorithm determines positional information of eye movement to determine gaze preference, skew deviation, abnormal fixation, and nystagmus.

7. The system of claim 1, further comprising calculating gaze-related information such as angle, velocities, and symmetries using an eyeball model and determining abnormal movements by positional tracking.

8. The system of claim 1, wherein facial landmarks include face and eye positions.

9. The system of claim 1, further comprising feeding extracted facial landmarks to at least one of a support vector machine classifier, penalized linear discriminant analysis classifier, k-nearest neighbors classifier, shallow neural networks classifier, deep neural networks classifier, and other classifiers for gaze-deviation and face and limb weakness detection.

10. A method for predicting the presence of one or more neurological deficits, comprising:

extracting audio information including a period density entropy coefficient and a mel frequency cepstral coefficient from an audio feed;
determining position and depth information of eye movement from a video feed;
detecting features of interest including facial landmarks, spatial orientation of limbs, and positional information of limb movement from the video feed;
extracting the features of interest from the video feed;
processing the extracted features of interest by aligning the features of interest to a common reference;
generating a set of coordinates representing the features of interest;
generating intensity-based features including a histogram of oriented gradients representing the extracted features of interest;
providing the audio information, the position and depth information of eye movement, the set of coordinates representing the features of interest, and the intensity-based features to a predictive model to classify the audio information, the position and depth information of eye movement, the set of coordinates representing the features of interest, and the intensity-based features; and
in response to the classification, predicting a presence of one or more neurological deficits.

11. The method of claim 10, wherein a smart phone, tablet, laptop, desktop, smart mirror, or mobile device is used to perform the method.

12. The method of claim 10, further comprising one or more processors configured to execute instructions to perform the method and wherein the instructions include a set of machine learning algorithms.

13. The method of claim 10, wherein the one or more neurological deficits include at least one of asymmetric smile, asymmetric eyebrow raise, limb ataxia, limb drift, pronator drift, nystagmus, or stroke information including type of stroke and location of stroke.

14. The method of claim 10, wherein extracting audio information includes detecting speech pathology including at least one of speech disturbance and language disturbance.

15. The method of claim 10, wherein a tracking algorithm determines positional information of eye movement to determine gaze preference, skew deviation, abnormal fixation, and nystagmus.

16. The method of claim 10, further comprising calculating gaze-related information such as angle, velocities, and symmetries using an eyeball model and determining abnormal movements by positional tracking.

17. The method of claim 10, wherein facial landmarks include face and eye positions.

18. The method of claim 10, further comprising feeding extracted facial landmarks to at least one of a support vector machine classifier, penalized linear discriminant analysis classifier, k-nearest neighbors classifier, shallow neural networks classifier, deep neural networks classifier, and other classifiers for gaze-deviation and face and limb weakness detection.

19. A non-transitory computer-readable medium storing instructions that, when executed by one or more processors, cause the one or more processors to perform operations for predicting presence of one or more neurological deficits, comprising:
extracting audio information including a period density entropy coefficient and a mel frequency cepstral coefficient from an audio feed;
determining position and depth information of eye movement from a video feed;
detecting features of interest including facial landmarks, spatial orientation of limbs, and positional information of limb movements from the video feed;
extracting the features of interest from the video feed;
processing the extracted features of interest by aligning the extracted features of interest to a common reference;
generating a set of coordinates representing the features of interest;
generating intensity-based features including a histogram of oriented gradients representing the extracted features of interest;
providing the audio information, the position and depth information of eye movement, the set of coordinates representing the features of interest, and the intensity-based features to a predictive model to classify the audio information, the position and depth information of eye movement, the set of coordinates representing the features of interest, and the intensity-based features; and
in response to the classification, predicting a presence of one or more neurological deficits.

20. The non-transitory computer-readable medium of claim 19, wherein the non-transitory computer-readable medium is a smart phone, tablet, laptop, desktop, smart mirror, or mobile device.

* * * * *